United States Patent
Lee et al.

(10) Patent No.: US 6,348,632 B1
(45) Date of Patent: Feb. 19, 2002

(54) PROCESS FOR PREPARING 1,3-ALKANEDIOL FROM EPOXIDE DERIVATIVE

(75) Inventors: Byeong-No Lee, Seoul; Byung-Soon Chen, Taejeon, both of (KR)

(73) Assignee: Samsung Electronics Co. Ltd., Kyungki-Do (KR)

( * ) Notice: Subject to any disclaimer, the term of this patent is extended or adjusted under 35 U.S.C. 154(b) by 0 days.

(21) Appl. No.: 09/570,012

(22) Filed: May 12, 2000

(30) Foreign Application Priority Data

Feb. 3, 2000 (KR) .............................................. 00-5357

(51) Int. Cl.$^7$ ............................................. C07C 27/00
(52) U.S. Cl. ...................................... 568/867; 568/864
(58) Field of Search .................................. 568/867, 864

(56) References Cited

U.S. PATENT DOCUMENTS

| | | | |
|---|---|---|---|
| 4,973,741 A | 11/1990 | Beavers ...................... | 560/279 |
| 5,043,480 A * | 8/1991 | Beavers ...................... | 568/496 |
| 5,135,901 A | 8/1992 | Beavers ...................... | 502/161 |
| 5,310,948 A | 5/1994 | Drent et al. ................ | 549/328 |
| 5,359,081 A | 10/1994 | Drent et al. ................ | 549/328 |
| 5,723,389 A | 3/1998 | Slaugh et al. ............... | 468/862 |
| 5,731,478 A | 3/1998 | Slaugh et al. ............... | 568/862 |
| 5,770,776 A | 6/1998 | Powell et al. ............... | 568/862 |
| 6,191,321 B1 * | 2/2001 | Forschner et al. .......... | 568/864 |

OTHER PUBLICATIONS

Herbert O. House, Modern Synthetic Reactions, 1972, W.A. Benjamine, p. 7.*

Enrico Dalcanale, et. al. A New Synthesis of 2–(Methoxycarbonylhexyl)–Cyclopent–2–En–1–One, 1986, pp. 492–493.

Richard F. Heck, The Reaction of Epoxides with Cobalt Hydrocarbonyl and Cobalt Tetracarbonyl Anion, Nov. 16, 1962, pp. 1460–1463.

John L. Eisenmann, et al. Preparation of Methyl β–Hydroxybutyrate from Propylene, etc.. Oct. 1960, pp. 2102–2105.

* cited by examiner

Primary Examiner—Johann Richter
Assistant Examiner—J. Parsa
(74) Attorney, Agent, or Firm—The Law Offices of Eugene M. Lee, PLLC

(57) ABSTRACT

A process for preparing an 1,3-alkanediol through carbonylation of an epoxide derivative includes the steps of (a) reacting an epoxide derivative with alcohol and carbon monoxide in a solvent at a temperature from about 30 to about 150° C. and at a pressure from about 50 to about 3000 psig in the presence of a catalyst system including an effective amount of a cobalt catalyst and an effective amount of a promoter to afford a reaction mixture including a 3-hydroxyester or derivative thereof in an amount of from 2 to about 95% by weight, (b) separating the reaction product and solvent from the catalyst and promoter, (c) reacting said reaction product and solvent with hydrogen at a temperature from about 30 to about 350° C. and at a pressure from about 50 to about 5000 psig in the presence of a catalyst system for hydrogenation to prepare a hydrogenation product mixture including a 1,3-alkanediol, and (d) recovering the 1,3-alkanediol from the hydrogenation product mixture. Catalyst systems for carrying out the inventive processes are also provided.

20 Claims, No Drawings

PROCESS FOR PREPARING 1,3-ALKANEDIOL FROM EPOXIDE DERIVATIVE

FIELD OF THE INVENTION

The present invention relates to a process for preparing a 1,3-alkanediol through carbonylation of an epoxide derivative. More specifically, the present invention relates to a process for preparing a 1,3-alkanediol, which comprises reacting an epoxide derivative with an alcohol and carbon monoxide in the presence of a catalyst system including a cobalt catalyst and a promoter to afford a 3-hydroxyester, and adding hydrogen to the 3-hydroxyester to prepare the 1,3-alkanediol.

BACKGROUND OF THE INVENTION

An epoxide derivative can be easily converted into a difunctional compound through carbonylation, which is used as an intermediate for preparing an organic compound. In particular, a 3-hydroxyester derivative has two functional groups, and is used as a solvent, a resin, a coating material, a material for medical substances, an intermediate for preparing alkanediols which are used for preparing polyesters, etc. The alkanediols are used as intermediates for coating materials or synthetic organic compounds. A 1,3-diol is an example of an alkanediol. As shown in the following scheme, a 1,3-diol is prepared by hydroformylating an epoxide derivative to prepare a 3-hydroxyaldehyde derivative and adding hydrogen to the 3-hydroxyaldehyde derivative to convert the aldehyde groups into alcohol groups.

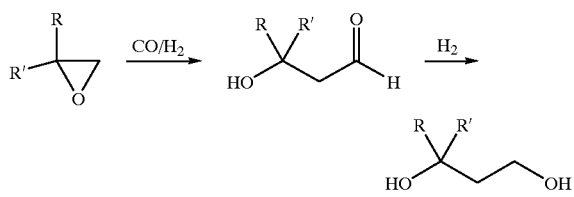

The scheme for preparing a 1,3-diol set forth above was disclosed in U.S. Pat. Nos. 5,770,776; 5,723,389; and 5,731,478. On the other hand, in a known process for synthesizing a 3-hydroxyaldehyde showing a high selectivity under low temperature and low pressure, there are used a cobalt catalyst and phosphine oxide ligand as a promoter. However, when phosphine oxide ligand is used as a promoter, the recovery and regeneration of the catalyst become complicated.

U.S. Pat. No. 5,770,776 discloses a process for preparing 1,3-propanediol comprising the steps of (a) contacting ethylene oxide with carbon monoxide and hydrogen in a non-water-miscible solvent in the presence of an effective amount of a non-phosphine-ligated cobalt catalyst and an effective amount of a catalyst promoter, (b) adding an aqueous liquid to the intermediate product mixture and extracting into the aqueous liquid a major portion of the 3-hydroxypropanal so as to provide a first aqueous phase and a first organic phase, (c) separating the first aqueous phase from the first organic phase, (d) adding fresh non-water-miscible solvent to the first aqueous phase and extracting into such solvent a portion of any cobalt catalyst or cobalt-containing derivative thereof present in such aqueous phase, to provide a second aqueous phase and a second organic phase, (e) separating the second aqueous phase from the second organic phase, (f) passing the first organic phase and the second organic phase to the process step (a), (g) contacting the second aqueous phase with hydrogen, and (h) recovering 1,3-propanediol.

U.S. Pat. Nos. 5,723,389 and 5,731,478 disclose a process for preparing an alkanediol comprising the steps of (a) contacting an ethylene oxide with carbon monoxide and hydrogen in a non-water-miscible solvent in the presence of an effective amount of a non-phosphine-ligated cobalt or rhodium catalyst and an effective amount of a cobalt or rhodium porphyrin promoter, (b) adding an aqueous liquid to the intermediate product mixture and extracting into the aqueous liquid a major portion of the hydroxyaldehyde so as to provide an aqueous phase and an organic phase, (c) separating the aqueous phase from the organic phase, (d) contacting the aqueous phase with hydrogen in the presence of a hydrogenation catalyst, and (e) recovering the alkanediol.

U.S. Pat. Nos. 5,135,901 and 4,973,741 disclose another process for obtaining the 3-hydroxyester derivative from the epoxide derivatives. In this process, there is synthesized methyl 3-hydroxypropionate from ethylene oxide by using rhodium and ruthenium as catalysts in the presence of carbon monoxide and alcohol. However, in this process, in spite of the use of expensive catalysts, the yield of the 3-hydroxypropionate is as low as 60%, and by-products are produced in considerable amounts. Further, there is another known process for obtaining a 3-hydroxyester by hydroesterification of the epoxide. In this process also, the yield is as low as 40–60% [(1) Dalcanali, E.; Foa, M. Synthesis 1986, 492. (2) Heck, R. F., J. Am. Chem. Soc., 1963, 85, 1460. (3) Eismann, J. L.; Yamartino, R. L.; Howard, Jr. J. F., J. Org. Chem. 1961, 2102.]. The reason why the yield is so low is that the isomerization reaction of the starting material readily occurs.

Meanwhile, U.S. Pat. Nos. 5,310,948 and 5,359,081 relate to carbonylation of the epoxide, in which the epoxide and carbon monoxide are reacted in the presence of cobalt and pyridine derivatives. The final product is mainly β-lactone, and the by-product is the 3-hydroxyester.

In the preparation of 1,3-alkanediols for preparing polyesters, if a 3-hydroxyaldehyde is used an intermediate, the quality of the polyester becomes lower because of formation of oligomers and acetals as by-products. On the other hand, if a 3-hydroxyester is used an intermediate, the yield will be lower yield and the catalyst cost will be high.

An effective catalyst system for preparing a 3-hydroxyester derivative from an ethylene oxide through hydroesterification has not been developed yet, and a method of obtaining a 1,3-alkanediol in a high yield has not been developed yet.

SUMMARY OF THE INVENTION

One feature of the present invention is the provision of a novel process for preparing a 1,3-alkanediol, which comprises reacting an epoxide derivative with an alcohol and carbon monoxide in the presence of a catalyst system that includes a cobalt catalyst and a promoter to afford a 3-hydroxyester, and adding hydrogen to the 3-hydroxyester to prepare the 1,3-alkanediol.

Another feature of the invention is the provision of a new catalyst system for preparing 3-hydroxyesters in a high yield by reacting an epoxide derivative with an alcohol and carbon monoxide, which catalyst system includes a cobalt catalyst and an imidazole or a derivative thereof as promoter.

A further feature of the invention is the provision of a process for preparing a 1,3-alkanediol, using a new catalyst system as described herein.

Still another feature of the invention is the provision of a process for preparing 1,3-alkanediols at a lower cost by using an imidazole or a derivative thereof as promoter.

In accordance with one aspect of the present invention, there is provided a process for preparing a 1,3-alkanediol through carbonylation of an epoxide derivative, which includes the steps of (a) reacting an epoxide derivative with an alcohol and carbon monoxide in a solvent at a temperature from about 30 to about 150° C. and at a pressure from about 50 to about 3000 psig in the presence of a catalyst system including an effective amount of a cobalt catalyst and an effective amount of a promoter to afford a reaction product including at least one 3-hydroxyester or derivative thereof in an amount from about 2 to about 95% by weight, (b) separating the reaction product and solvent from the catalyst and promoter, (c) reacting the reaction product and solvent with hydrogen at a temperature from about 30 to about 350° C. and at a pressure from about 50 to about 5000 psig in the presence of a catalyst system for hydrogenation to prepare a hydrogenation product mixture including a 1,3-alkanediol, and (d) recovering the 1,3-alkanediol from the hydrogenation product mixture.

In accordance with another aspect of the present invention, a catalyst system for preparing a 1,3-alkanediol as described herein is provided.

Other objects, features and advantages of the present invention will become apparent it to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Korean patent application number 2000-5357, filed on Feb. 3, 2000 and entitle "Process for Preparing 1,3-Alkanediol from Epoxide Derivative" is incorporated by reference herein in its entirety.

The present inventors have developed a process for preparing a 1,3-alkanediol in a high yield by synthesizing a 3-hydroxyester as an intermediate from an epoxide derivative through hydroesterification, and then reacting the 3-hydroxyester with hydrogen and a catalyst system for hydrogenation.

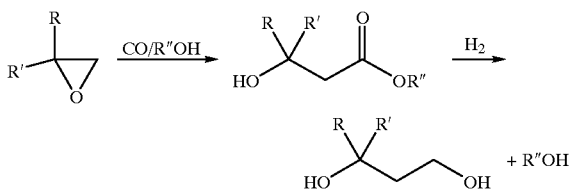

The present invention thus relates to a process for preparing a 1,3-alkanediol through carbonylation of an epoxide derivative. An epoxide derivative reacts with an alcohol and carbon monoxide in a solvent at a temperature from about 30 to about 150° C. and at a pressure from about 50 to about 3000 psig in the presence of a catalyst system including an effective amount of a cobalt catalyst and an effective amount of a promoter to afford a reaction product including at least one 3-hydroxyester or derivative thereof in an amount from about 2 to about 95% by weight. In this invention, this step is called "hydroesterification". The reaction product and solvent are separated from the catalyst and promoter. The reaction product and solvent react with hydrogen at a temperature from about 30 to about 350° C. and at a pressure from about 50 to about 5000 psig in the presence of a catalyst system for hydrogenation to prepare a hydrogenation product mixture including a 1,3-alkanediol. In this invention, this step is called "hydrogenation". The 1,3-alkanediol is recovered from the hydrogenation product mixture.

In the present invention, an effective catalyst system is employed to maximize the production yield of the 3-hydroxyester when an epoxide derivative undergoes the hydroesterification. The catalyst system includes a cobalt catalyst and a catalyst promoter. The cobalt catalyst can be, for example, $Co_2(CO)_8$, or a mixture of $Co_2(CO)_8$ and an organic compound. The organic compound preferably, is selected from the group consisting of imidazole, pyridine, pyrrole, pyrazine, pyrimidine, piperidine, a derivative thereof, and a mixture thereof. It is preferable to use an organic compound which is not bonded to a phosphine compound.

Preferably, an imidazole derivative as shown in the following formula (I) is used as a promoter:

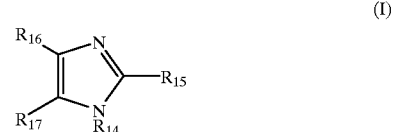

(I)

where $R_{14}$, $R_{15}$, $R_{16}$ and $R_{17}$ independently are hydrogen; branched aliphatic hydrocarbon having 3 to 10 carbon atoms; linear aliphatic hydrocarbon having 1 to 10 carbon atoms; saturated cyclohydrocarbon having 3 to 10 carbon atoms; cycloaliphatic hydrocarbon having 3 to 10 carbon atoms; aromatic aliphatic hydrocarbon having 7 to 10 carbon atoms; F; Cl; alkoxy having 1 to 3 carbon atoms; OH; OH group-containing branched aliphatic hydrocarbon having 3 to 10 carbon atoms; OH group-containing linear aliphatic hydrocarbon having 1 to 10 carbon atoms; OH group-containing saturated cyclohydrocarbon having 3 to 10 carbon atoms; OH group-containing cycloaliphatic hydrocarbon having 3 to 10 carbon atoms; or OH group-containing aromatic aliphatic hydrocarbon having 7 to 10 carbon atoms.

It is preferable to use the cobalt catalyst and promoter in a ratio between about 1:0.01 and about 1:100.

An appropriate solvent is used in the hydroesterification in the presence of alcohol. The hydroesterification is carried out at a temperature from about 30 to about 150° C., preferably from about 40 to about 120° C. and at the CO pressure from about 50 to about 3000 psig, preferably from about 100 to about 1500 psig.

The epoxide derivative usable in this invention is shown as the following formula (II):

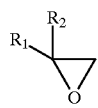

(II)

where in $R_1$ and $R_2$ independently are hydrogen; linear aliphatic hydrocarbon having 1 to 20 carbon atoms; branched aliphatic hydrocarbon having 3 to 20 carbon atoms; saturated cycloaliphatic hydrocarbon having 3 to 20 carbon atoms; cycloaliphatic hydrocarbon having 3 to 20 carbon atoms; aromatic aliphatic hydrocarbon having 7 to 20 carbon atoms; hydrocarbon having 1 to 20 carbon atoms in which a hydrogen on the carbon chain is substituted with F, Cl or Br; aromatic hydrocarbon having 6 to 20 carbon atoms with no substituted group; or aromatic hydrocarbon having 6 to 20 carbon atoms in which a hydrogen on the aromatic ring is substituted with F, Cl, an amine group, a nitrile group, or an alkoxy group.

Particular preferred examples of epoxide derivatives useful according to the invention include ethylene oxide, propylene oxide, 1-butene oxide, 1-pentene oxide, 1-heptene oxide, 1-octene oxide, 1-nonene oxide, 1-decene oxide, 2-methyl-propylene oxide, 2-methyl-1-butene oxide, 2-methyl-1-octene oxide, 2-methyl-nonene oxide, 2-methyl-1-decene oxide, 2-methyl-1-butene oxide, 2-methyl-1-pentene oxide, 2-methyl-1-hexene oxide, 2-methyl-1-heptene oxide, 2-ethyl-1-octene oxide, 2-ethyl-1-nonene oxide, 2-ethyl-1-decene oxide, epifluorohydrin, epichlorohydrin, epibromohydrin, glycidol, methyl glycidate, ethyl glycidate, t-butyl glycidate, allyl benzene oxide, styrene oxide, etc.

The alcohol of the present invention is expressed by R'OH. Here, R' is a saturated linear hydrocarbon having 1 to 20 carbon atoms, an unsaturated linear hydrocarbon having 2 to 20 carbon atoms, a branched hydrocarbon having 3 to 20 carbon atoms, a cyclohydrocarbon having 3 to 20 carbon atoms, an aromatic hydrocarbon having 6 to 20 carbon atoms, or a linear hydrocarbon including an aromatic group. Preferably R' is methyl, ethyl, isopropyl, cyclohexyl, phenyl or benzyl.

The solvent of the present invention can be an ether, a substituted aromatic compound, or an acetate. Of course, the alcohol itself can be used as a solvent.

The ethers useful according to the invention include those represented by the following formulas (III), (IV) and (V):

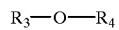

(III)

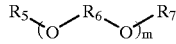

(IV)

(V)

where $R_3$, $R_4$, $R_5$, $R_6$, and $R_7$ independently are saturated aliphatic hydrocarbon having 1 to 10 carbon atoms having no branches; branched aliphatic hydrocarbon having 3 to 10 carbon atoms; saturated cyclohydrocarbon having 3 to 10 carbon atoms; cycloaliphatic hydrocarbon having 3 to 10 carbon atoms; or aromatic aliphatic hydrocarbon having 7 to 10 carbon atoms; m is an integer of 1 to 10; and n is an integer of 2 to 5.

Substituted aromatic compounds useful according to the invention include those represented by the following formula (VI):

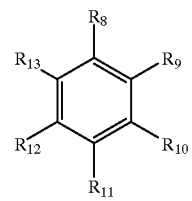

(VI)

where $R_8$, $R_9$, $R_{10}$, $R_{11}$, $R_{12}$ and $R_{13}$ independently are hydrogen; saturated aliphatic hydrocarbon having 1 to 4 carbon atoms having no branches; branched aliphatic hydrocarbon having 3 or 4 carbon atoms; F; Cl; or alkoxy group having 1 to 3 carbon atoms.

3-hydroxyesters and derivatives thereof are obtained through hydroesterification of the epoxide derivative. The 3-hydroxyesters and derivatives thereof afforded according to the present invention are represented by the following formulas (VII) and (VIII):

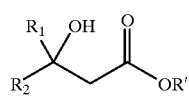

(VII)

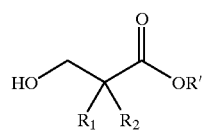

(VIII)

where $R_1$ and $R_2$ independently are hydrogen; linear aliphatic hydrocarbon having 1 to 20 carbon atoms; branched aliphatic hydrocarbon having 3 to 20 carbon atoms; saturated cycloaliphatic hydrocarbon having 3 to 20 carbon atoms; cycloaliphatic hydrocarbon having 3 to 20 carbon atoms; aromatic aliphatic hydrocarbon having 7 to 20 carbon atoms; hydrocarbon having 1 to 20 carbon atoms in which a hydrogen on the carbon chain is substituted with F, Cl or Br; aromatic hydrocarbon having 6 to 20 carbon atoms with no substituted group; or aromatic hydrocarbon having 6 to 20 carbon atoms in which a hydrogen on the aromatic ring is substituted with F, Cl, an amine group, a nitrile group, or an alkoxy group, and R' is a saturated linear hydrocarbon having 1 to 20 carbon atoms, an unsaturated linear hydrocarbon having 2 to 20 carbon atoms; a branched hydrocarbon having 3 to 20 carbon atoms; a cyclohydrocarbon having 3 to 20 carbon atoms; an aromatic hydrocarbon having 6 to 20 carbon atoms, or a linear hydrocarbon including an aromatic group.

As shown in formulas (VII) and (VIII), the 3-hydroxyesters and derivatives thereof are difunctional so as to be available as an intermediate for synthesizing an organic compound or for a coating material.

The reaction product and solvent are separated from the catalyst and promoter. The separation of the reaction product and solvent preferably is carried out by vacuum distillation or by extracting into water, which will depend on the solvent. When an ether of Formula (III) or a substituted aromatic compound of Formula (IV) is used as solvent, the reaction product of 3-hydroxyester derivative is extracted into water. When an ether of Formula (IV) or (V) or a lower alcohol such as methyl alcohol, ethyl alcohol or isopropyl alcohol is used as solvent, the reaction product is separated under vacuum distillation. When a higher alcohol than isopropyl alcohol is used as solvent, the reaction product is separated by extracting into water. When extracting into water, the 3-hydroxyesters and derivatives thereof are extracted into the water layer by adding water at about 100° C. or lower to the reaction production mixture in the presence of carbon monoxide at a pressure from about 20 to about 3000 psig.

The extracts react with hydrogen at a temperature from about 30 to about 350° C. and at pressure from about 50 to about 5000 psig in the presence of a catalyst system for hydrogenation to prepare a hydrogenation product mixture including a 1,3-alkanediol. In this invention, this step is called "hydrogenation". The hydrogenation can be carried out without extraction of the reaction products. The separated catalyst and promoter can be recycled to the hydroesterification step in part or in total.

The 3-hydroxyester derivative is hydrogenated in the presence of a catalyst system to produce a 1,3-alkanediol. The catalyst system for the hydrogenation preferably includes copper chromate or Pd/C.

The hydrogenation process preferably is carried out at a temperature from about about 50 to about 250° C. and at a pressure from about 200 to about 3000 psig.

Finally, the 1,3-alkanediol is recovered from the hydrogenation product mixture. The separation and hydrogenation of the reaction product can be easily carrier out by an ordinary skilled person in the art to which the present invention pertains.

The present invention is further illustrated by the following non-limiting examples.

EXAMPLES

Examples 1–10

Hydroesterification of Ethylene Oxide with Catalyst of $Co_2(CO)_8$ in Imidazole At room temperature, a 450 ml Parr reactor was filled with methanol and 5 mmole of $Co_2(CO)_8$. The reactor was filled with CO gas at 500 psig, heated to 80° C. and agitated for one hour. Then the reactor was cooled to room temperature and imidazole as promoter was added to the reactor. Ethylene oxide was added to the reactor and CO was added at a predetermined pressure. The reactor was heated to a temperature as shown in Table 1 at a pressure as in Table 1 for the time as in Table 1. During the reaction, the reaction product was sampled using a tube. As product, methyl 3-hydroxypropionate (3-HPM) was analyzed with a GC. The reaction conditions and the resulting data are shown in Table 1.

Imidazole of 20 mmole as promoter was used in Examples 1–7 and 9, 40 mmole in Example 8, and 30 mmole in Example 10. Ethylene oxide of 500 mmole was used in Examples 1–8 and 10, and 1.4 mmole in Example 9. In Example 7, tetraglyme was used besides methyl alcohol.

TABLE 1

| Example | Temp. (° C.) | Pressure (bar) | Time (hrs) | MeOH (ml) | Conversion Rate(%) | Yield[1](%) 3-HPM | Selectivity(mole %) 3-HPM[2] | AA[3] | DMA[4] | ME[5] | Dimer[6] |
|---|---|---|---|---|---|---|---|---|---|---|---|
| 1 | 70 | 34 | 3 | 200 | 78.09 | 65.66 | 84.08 | 2.71 | 9.44 | 1.10 | 2.66 |
| 2 | 70 | 50 | 3 | 200 | 68.23 | 59.68 | 87.47 | 7.77 | 0.20 | 2.38 | 2.17 |
| 3 | 70 | 80 | 3 | 200 | 65.66 | 58.65 | 89.33 | 4.50 | 0.59 | 2.47 | 3.11 |
| 4 | 60 | 50 | 3 | 200 | 45.19 | 40.20 | 88.96 | 8.45 | 0.39 | 2.19 | 0 |
| 5 | 75 | 50 | 3 | 200 | 78.62 | 66.01 | 83.97 | 0.03 | 10.98 | 1.92 | 3.10 |
| 6 | 80 | 50 | 3 | 200 | 91.61 | 71.86 | 78.45 | 9.44 | 6.51 | 2.63 | 2.97 |
| 7 | 80 | 34 | 2 | 100 | — | 82.44 | — | — | — | — | — |
| 8 | 80 | 34 | 4 | 250 | — | 70.1 | — | — | — | — | — |
| 9 | 80 | 34 | 4 | 200 | — | 66.4 | — | — | — | — | — |
| 10 | 75 | 60 | 3 | 150 | 95.27 | 88.90 | 93.31 | 1.78 | 0.32 | 0.98 | 3.61 |

Notes:
[1]Yield = Selectivity X Conversion rate
[2]3-HPM: methyl 3-hydroxypropionate(3hydroxypropionic acid methyl ester)
[3]AA: acetaldehyde
[4]DMA: acetaldehyde dimethyl acetal
[5]ME: methoxy ethanol
[6]Dimer: $HOCH_2CH_2C(O)OCH_2CH_2(O)OCH_3$

Comparative Examples 1–2

Hydroesterification of Ethylene Oxide with Catalyst of $Co_2(CO)_8$

Comparative Example 1 was conducted in the same manner as in Example 1 except that 4 mmole of 3-hydroxypyridine was used as promoter instead of imidazole and except the reaction conditions. 1 mmole of $Co_2(CO)_8$ was used and 200 mmole of ethylene oxide was used. The reaction conditions of Comparative Example 1 were shown in Table 2.

Comparative Example 2 was conducted in the same manner as in Example 1 except that $Co_2(CO)_8$ as catalyst was used without any catalyst promoter. 2.5 mmole of $Co_2(CO)_8$ was used and 650 mmole of ethylene oxide was used. The reaction conditions of Comparative Example 2 were shown in Table 2. the resulting data were shown in Table 2.

In Comparative Example 1 using a pyridine derivative, 3-HPM was obtained in a high yield, but by-products such as acetaldehyde were produced in a significant amount. In Comparative Example 2 not using a catalyst promoter, the yield of 3-HPM was very low.

TABLE 2

| Comparative Example | Temp. (° C.) | Pressure (bar) | Time (hrs) | MeOH (ml) | Conversion Rate(%) | Yield[1](%) 3-HPM | Selectivity(mole %) | | | | |
|---|---|---|---|---|---|---|---|---|---|---|---|
| | | | | | | | 3-HPM[2] | AA[3] | DMA[4] | ME[5] | Dimer[6] |
| 1 | 75 | 60 | 4 | 40 | 92.07 | 81.08 | 88.07 | 8.43 | — | 2.28 | 1.22 |
| 2 | 75 | 60 | 4 | 120 | — | 20.6 | — | — | — | — | — |

Notes:
[1] Yield = Selectivity X Conversion rate
[2] 3-HPM: methyl 3-hydroxypropionate (3-hydroxypropionic acid methyl ester)
[3] AA: acetaldehyde
[4] DMA: acetaldehyde dimethyl acetal
[5] ME: methoxy ethanol
[6] Dimer: $HOCH_2CH_2C(O)OCH_2CH_2(O)OCH_3$

Examples 11–14

Examples 11–14 were conducted in the same manner as in Example 1 except for use of the epoxide derivative. As shown in Table 3, in Examples 11–14, propylene oxide, butylenes oxide, epichlorohydrin, and glycidol as epoxide derivative were used, respectively. 5 mmole of $Co_2(CO)_8$, 10 mmole of catalyst promoter, 500 mmole of epoxide derivative, and 200 ml of ethyl alcohol as solvent were used. The reactor was kept a 80° C. and at 34 bar for 4 hours. The products and yields of Examples 11–14 are show in Table 3.

TABLE 3

| Example | Epoxide | Product | Yield (%) |
|---|---|---|---|
| 1 | propylene oxide | methyl 3-hydroxybutanoate | 60.56 |
| 2 | butylene oxide | methyl 3-hydroxypentanoate | 53.70 |
| 3 | epichlorohydrin | methyl 3-hydroxy4-chloro-butanoate | 66.17 |
| 4 | glycidol | 3-hydroxy γ-butyrolacton | 62.50 |

Example 15

1 g of 3-hydroxypropionate was added to a 45 ml Parr reactor together with 10 ml of methyl alcohol as a solvent for the 3-hydroxypropionate. 0.5 g of copper chromate was added to the reactor as a catalyst. Hydrogen was introduced to the reactor at 1500 psig and the reactor was agitated and heated to 180° C. After reaction for 15 hours, the reactor was cooled to room temperature. The product was analyzed with a GC. Conversion rate to 3-hydroxypropionate was about 5%, and selectivity to 1,3-propandiol was about 3%.

The present invention provides a novel process for preparing a 1,3-alkanediol, in which a 3-hydroxyester is prepared in a high yield by reacting an epoxide derivative with an alcohol and carbon monoxide in the presence of a catalyst system including a cobalt catalyst and a promoter, in particular an imidazole or a derivative thereof. Further, the present invention provides a process for preparing a 1,3-alkanediol at a lower cost by using an imidazole or a derivative thereof as promoter.

It should be apparent to those ordinarily skilled in the art that various changes and modifications can be made without departing from the scope of the present invention.

What is claimed is:

1. A process for preparing 1,3-alkanediol through carbonylation of an epoxide derivative, which comprises the steps of:
   (a) reacting an epoxide derivative with alcohol and carbon monoxide in a solvent at a temperature from about 30 to about 150° C. and at a pressure from about 50 to about 3000 psig in the presence of a catalyst system comprising an effective amount of a cobalt catalyst and an effective amount of a promoter to afford a reaction product including at least one 3-hydroxyester or derivative thereof in an amount from about 2 to about 95% by weight, wherein the promoter is selected from the group consisting of imidazole, an imidazole derivative and a mixture thereof;
   (b) separating said reaction product and solvent from the catalyst and promoter;
   (c) reacting said reaction product and solvent with hydrogen at a temperature of from about 30 to about 350° C. and at a pressure from about 50 to about 5000 psig in the presence of a catalyst system for hydrogenation to prepare a hydrogenation product mixture comprising a 1,3-alkanediol; and
   (d) recovering said 1,3-alkanediol from said hydrogenation product mixture.

2. The process as claimed in claim 1, wherein said separating step (b) is conducted under vacuum distillation.

3. The process according to claim 1, wherein said separating step (b) comprises the steps of adding water at about 100° C. or lower to said reaction product, solvent, catalyst, and promoter in the presence of carbon monoxide at a pressure from about 20 to about 3000 psig and extracting said at least one 3-hydroxyester or derivative thereof into said water.

4. The process according claim 1, further comprises the step of recycling at least a portion of said catalyst and promoter to said reacting step (a).

5. The process as claimed in claim 1, wherein cobalt catalyst is $C_{o2}(CO)_8$ or a mixture of $Co2(CO)8$ and an organic compound selected from the group consisting of imidazole, an imidazole derivative and a mixture thereof.

6. The process as claimed in claim 1, wherein said cobalt catalyst and promoter are employed at the ratio between about 1:0.01 and about 1:100.

7. The process as claimed in claim 1, wherein said promoter is represented by the following formula (I):

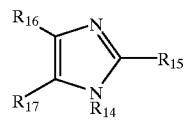

(I)

where $R_{14}$, $R_{15}$, $R_{16}$ and $R_{17}$ independently are hydrogen; branched aliphatic hydrocarbon having 3 to 10 carbon atoms; linear aliphatic hydrocarbon having 1 to 10 carbon atoms; saturated cyclohydrocarbon having 3 to 10 carbon atoms; cycloaliphatic hydrocarbon having 3 to 10 carbon atoms; aromatic aliphatic hydrocarbon having 7 to 10 carbon atoms; F; Cl; alkoxy having 1 to 3 carbon atoms; OH; OH group-containing branched aliphatic hydrocarbon having 3 to 10 carbon atoms; OH group-containing linear aliphatic hydrocarbon having 1 to 10 carbon atoms; OH group-containing saturated cyclohydrocarbon having 3 to 10 carbon atoms; OH group-containing cycloaliphatic hydrocarbon having 3 to 10 carbon atoms; or OH group-containing aromatic aliphatic hydrocarbon having 7 to 10 carbon atoms.

8. The process as claimed in claim 7, wherein said promoter is an imidazole.

9. The process as claimed in claim 1, wherein said step (a) is conducted at a temperature from about 40 to about 120° C.

10. The process as claimed in claim 1, wherein said step (a) is conducted at a pressure from about 100 to about 1500 psig.

11. The process as claimed in claim 1, wherein said epoxide derivative is represented by the following formula (II):

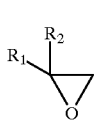

(II)

wherein $R_1$ and $R_2$ independently are hydrogen; linear aliphatic hydrocarbon having 1 to 20 carbon atoms; branched aliphatic hydrocarbon having 3 to 20 carbon atoms; saturated cycloaliphatic hydrocarbon having 3 to 20 carbon atoms; cycloaliphatic hydrocarbon having 3 to 20 carbon atoms; aromatic aliphatic hydrocarbon having 7 to 20 carbon atoms; hydrocarbon having 1 to 20 carbon atoms in which a hydrogen on the carbon chain is substituted with F, Cl or Br; aromatic hydrocarbon having 6 to 20 carbon atoms with no substituted group; or aromatic hydrocarbon having 6 to 20 carbon atoms in which a hydrogen on the aromatic ring is substituted with F, Cl, an amine group, a nitrile group, or an alkoxy group.

12. The process as claimed in claim 1, wherein said alcohol is represented by R'OH, wherein R' is a saturated linear hydrocarbon having 1 to 20 carbon atoms, an unsaturated linear hydrocarbon having 2 to 20 carbon atoms, a branched hydrocarbon having 3 to 20 carbon atoms, a cyclohydrocarbon having 3 to 20 carbon atoms, an aromatic hydrocarbon having 6 to 20 carbon atoms, or a linear hydrocarbon including an aromatic substituent.

13. The process as claimed in claim 1, wherein said solvent is represented by the following formula (III), (IV) or (V):

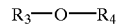

(III)

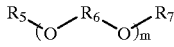

(IV)

(V)

where $R_3$, $R_4$, $R_5$, $R_6$, and $R_7$ independently are saturated aliphatic hydrocarbon having 1 to 10 carbon atoms having no branches; branched aliphatic hydrocarbon having 3 to 10 carbon atoms; saturated cyclohydrocarbon having 3 to 10 carbon atoms; cycloaliphatic hydrocarbon having 3 to 10 carbon atoms; or aromatic aliphatic hydrocarbon having 7 to 10 carbon atoms; m is an integer of 1 to 10; and n is an integer of 2 to 5.

14. The process as claimed in claim 1, wherein said solvent is an acetate.

15. The process as claimed in claim 1, wherein said solvent is an alcohol represented by R'OH, wherein R' is a saturated linear hydrocarbon having 1 to 20 carbon atoms, an unsaturated linear hydrocarbon having 2 to 20 carbon atoms, a branched hydrocarbon having 3 to 20 carbon atoms, a cyclohydrocarbon having 3 to 20 carbon atoms, an aromatic hydrocarbon having 6 to 20 carbon atoms, or a linear hydrocarbon including an aromatic substituent.

16. The process as claimed in claim 1, wherein said solvent is a substituted aromatic compound represented by the following formula (VI):

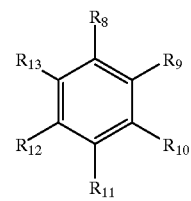

(VI)

where $R_8$, $R_9$, $R_{10}$, $R_{11}$, $R_{12}$ and $R_{13}$ independently are hydrogen; saturated aliphatic hydrocarbon having 1 to 4 carbon atoms having no branches; branched aliphatic hydrocarbon having 3 or 4 carbon atoms; F; Cl; or alkoxy group having 1 to 3 carbon atoms.

17. The process as claimed in claim 1, wherein said reaction product comprises at least one of a 3-hydroxyester and a derivative thereof represented by the following formulas (VII) and (VIII):

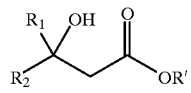

(VII)

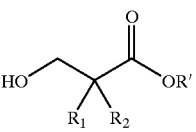

(VIII)

where $R_1$ and $R_2$ independently are hydrogen; linear aliphatic hydrocarbon having 1 to 20 carbon atoms; branched aliphatic hydrocarbon having 3 to 20 carbon atoms; saturated cycloaliphatic hydrocarbon having 3 to 20 carbon atoms; cycloaliphatic hydrocarbon having 3 to 20 carbon atoms; aromatic aliphatic hydrocarbon having 7 to 20 carbon atoms; hydrocarbon having 1 to 20 carbon atoms in which a hydrogen on the carbon chain is substituted with F, Cl or Br; aromatic hydrocarbon having 6 to 20 carbon atoms with no substituted group; or aromatic hydrocarbon having 6 to 20 carbon atoms in which a hydrogen on the aromatic ring is substituted with F, Cl, an amine group, a nitrile group, or an alkoxy group, and R' is a saturated linear hydrocarbon having 1 to 20 carbon atoms, an unsaturated linear hydrocarbon having 2 to 20 carbon atoms; a branched hydrocarbon having 3 to 20 carbon atoms; a cyclohydrocarbon having 3 to 20 carbon atoms; an aromatic hydrocarbon having 6 to 20 carbon atoms; or a linear hydrocarbon including an aromatic substituent.

18. The process as claimed in claim 1, wherein said catalyst system of said step (c) is selected from the group consisting of copper chromate and Pd/C.

19. The process as claimed in claim 1, wherein said step (c) is conducted at the pressure of hydrogen from about 200 to about 3000 psig.

20. The process as claimed in claim 1, wherein said step (c) is conducted at a temperature from about 50 to about 250° C.

* * * * *